(12) United States Patent
Liu et al.

(10) Patent No.: US 6,561,045 B2
(45) Date of Patent: May 13, 2003

(54) SAMPLER FOR ELIMINATING PARTICLE-RELATED ARTIFACTS FOR FLUE GAS MEASUREMENT

(75) Inventors: Benjamin Y. H. Liu, North Oaks, MN (US); Daryl L. Roberts, Blaine, MN (US); Virgil A. Marple, Maple Plain, MN (US); Francisco J. Romay, Vadnais Heights, MN (US)

(73) Assignee: MSP Corporation, Minneapolis, MN (US)

( * ) Notice: Subject to any disclaimer, the term of this patent is extended or adjusted under 35 U.S.C. 154(b) by 0 days.

(21) Appl. No.: 09/841,538

(22) Filed: Apr. 24, 2001

(65) Prior Publication Data

US 2001/0032519 A1 Oct. 25, 2001

Related U.S. Application Data

(60) Provisional application No. 60/200,153, filed on Apr. 26, 2000.

(51) Int. Cl.[7] ............................................. G01N 1/00
(52) U.S. Cl. ................................................... 73/863.21
(58) Field of Search ........................ 73/863.21, 863.22, 73/28.01, 28.04–28.06, 863.81, 863.83; 96/413

(56) References Cited

U.S. PATENT DOCUMENTS

| 3,289,481 A | * | 12/1966 | Barnes |
| 3,960,500 A | * | 6/1976 | Ross et al. ............... 73/863.81 |
| 4,133,202 A | | 1/1979 | Marple .......................... 73/28 |
| 4,321,822 A | | 3/1982 | Marple et al. .................. 73/28 |
| 4,670,135 A | | 6/1987 | Marple et al. .............. 509/143 |
| 4,767,524 A | | 8/1988 | Yeh et al. .................... 209/143 |
| 4,972,957 A | | 11/1990 | Liu et al. .................... 209/143 |
| 5,040,424 A | | 8/1991 | Marple et al. ........... 73/863.23 |
| 5,423,228 A | | 6/1995 | Budd et al. ............... 73/863.21 |

* cited by examiner

Primary Examiner—Robert R. Raevis
(74) Attorney, Agent, or Firm—Westman, Champlin & Kelly, P.A.

(57) ABSTRACT

A sampler for removing a sample of gas from a flue or stack utilizes virtual impactor principles, together with a gas jet ejector to insure that the surfaces are kept free of particles. The gas that is, discharged from the sampler thus is not changed in character by contact with particles that may adhere to surfaces of the sampler.

18 Claims, 5 Drawing Sheets

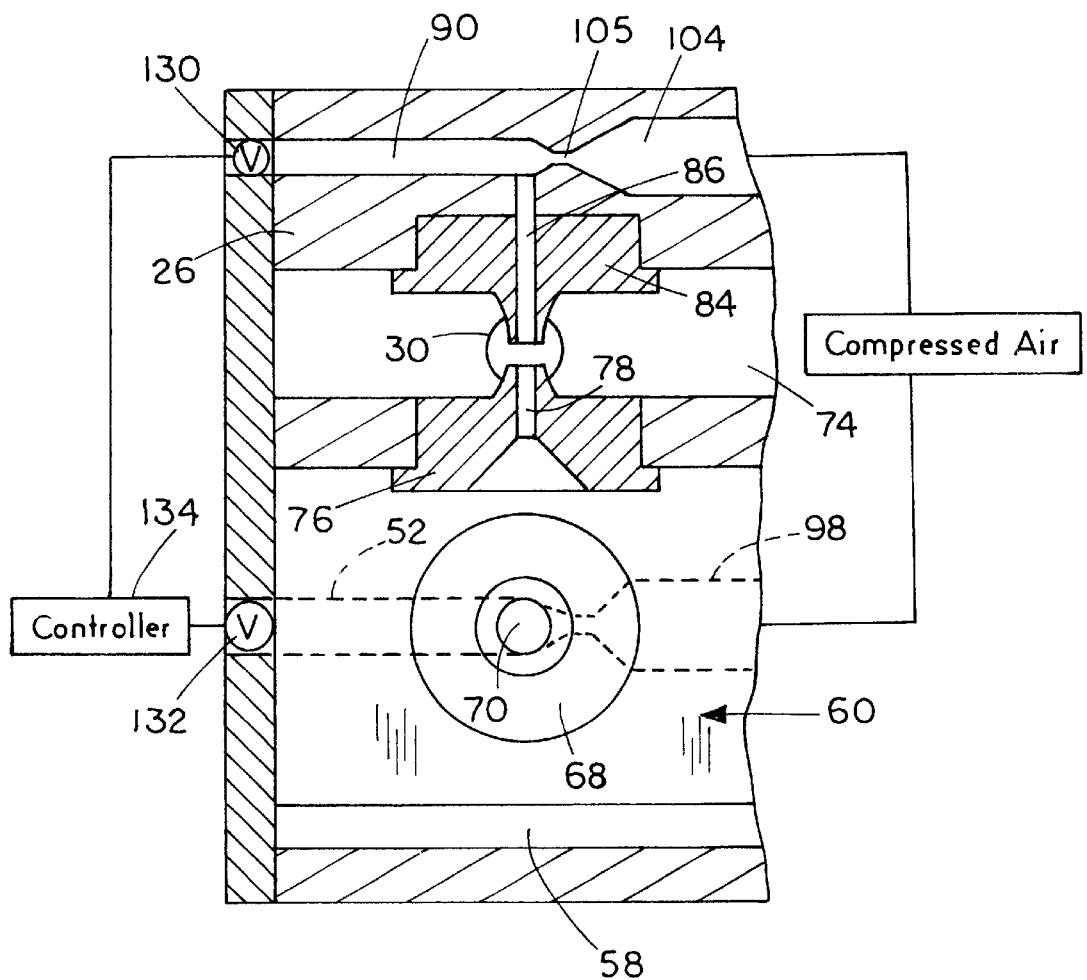

SAMPLER FOR ELIMINATING PARTICLE-RELATED ARTIFACTS FOR FLUE GAS MEASUREMENT

The present application is based on and claims the priority on U.S. provisional patent application Serial No. 60/200,153, filed Apr. 26, 2000, the content of which is hereby incorporated by reference in its entirety.

Developments described in this application were made in part under grant number DE-FG02-99ER86087 and the United States Government has certain rights to this invention.

BACKGROUND OF THE INVENTION

The present invention relates to a sampler that will remove flue gases from stacks, such as from coal fired power plants, and remove particulate matter from the gases so that the remaining sample can be analyzed accurately for the presence of mercury, in particular, as well as other gases.

Mercury is a significant environmental concern because of its toxicity, persistence, and bio-magnification in the food chain. The chemical form of mercury found in flue gases heavily influences its behavior in control devices and its environmental impact. Therefore, the measurement of mercury in its major chemical and physical forms in flue gases, preferably in real time, is central to efficient design of any mercury control device, to understanding the behavior of mercury in the environment, and to the rational regulation of mercury emissions. Various investigators have presented critical reviews of the importance and difficulty of making reliable measurements of the concentration and speciation of mercury in flue gases. There has been no sampler that insures that a sample of flue gas remains essentially unchanged as it traverses the sampling lines to the analyzer. Particulate matter in the flue gas affects the chemical form of mercury in such gas and its distribution between gaseous and particular components of flue gas. It is now recognized that separating out the particulate matter from the flue gas is a way of insuring that accurate sampling and analysis can take place.

In some instances, filters, cyclones, and cascade impactors will capture and even size fractionate particles in flue gases, and these have been shown to improve the quality of mercury data.

After a relatively short while, these devices reach their capacity for particles and have to be manually cleaned or replaced. Hence they are unsuitable for continuous and/or real time mercury monitoring in a commercial setting. One fundamental limitation of cyclones, impactors, filters, diffusion batteries, electrostatic precipitators and similar devices is that particles accumulate in these devices. Not only does the fresh flue gas pass over the accumulated particles, distorting the measurement of both the particle bound and gaseous mercury species, but the devices do have to be periodically cleaned.

In order to overcome these difficulties. The present invention discloses a variation of a virtual impactor for sampling flue gases, and removing particulate matter from a flow of gases provided to an analyzation instrument, such as a mercury Chemical Environmental Monitor (CEM). Virtual impactors, that have high capacity, are known for sampling particles in the atmosphere, for example, and U.S. Pat. No. 4,670,135 illustrates such a device.

SUMMARY OF THE INVENTION

The present invention relates to a sampler mounted within a flue for sampling flue gases and removing particulate material from a flow sample of the gas which is then provided to a an exterior chemical analyzation instrument. The removal of the particles insures that the gaseous chemicals, such as mercury, will not change species or concentration, because influences from the chemical makeup of the particles is removed.

The present invention uses an opposing jet virtual impactor concept, to disengage the particulate matter in the gas stream and accumulate no particulate matter in the sampling device itself. The virtual impactor in the preferred form has been modified to insure that the nozzles and flow passages used are maintained particle free substantially at all times. If it is desired that a cleaning cycle should be used, the cleaning can be done easily and automatically with compressed air and without replacement of components or parts.

The virtual impactor sampler reduces the pressure drop that is associated with many other samplers, and substantially reduces the inadvertent deposition of unwanted particles on the internal surfaces of sample. The virtual impactor uses inlet nozzles aligned with receiver nozzles or tubes into which particles are inertially discharged. While the major gas flow is diverted to a separate flow path, the sampler has two stages of particle separation, in a preferred embodiment shown. The use of a single stage is feasible where there is a low loading of tale sample, and the additional second stage insures the virtual impactor is useable with both high loading and low loading applications and a wide range of flue gas particle size distributions. The sampler is quite compact, and it can be mounted in the flue or stack. The outlet from the sampler for the cleaned or particle free gas is connected to a pump that caused a flow of the gas sample through the analyzation instrument, or mercury CEM that is used in the disclosed embodiment.

The cleaning of the sampler is achieved by utilizing compressed air jets in the exhaust passageways in the sampler body that carry the removed particles from receiver tubes. A high velocity jet flows across receiver passageways that carry the inertially separated particles, insuring that the particles will be discharged immediately and under sufficient pressure to avoid deposition of the particles on passageway surfaces, or on components of the virtual impactor. The jet causes a minor flow of gas through the receiver tubes.

A second form of the invention can be used with valves in the particle exhaust passageways that will close momentarily so that the compressed air will backflush the receiver passageways and if desired the inlet nozzles and passageways of the virtual impactor.

The analyzation instrument can be any desired conventional instrument. The virtual impactor sampler provides a substantially particle free gas for analyzation so that accurate determinations of the chemicals being analyzed is obtained.

In operation, it has been found that the virtual impactor of the present invention accumulates no significant particulate matter and leaves both elemental mercury and mercury chloride unperturbed when sampling flue gases.

The impactor is capable of operating under elevated temperatures, that are commonly found in coal fired power plant stacks or flues, for example, temperatures in the range of 300° F. can be handled. The compressed air that is utilized for providing jets for maintaining the virtual impactor free of particles is generally readily available in coal fired power plants, but if necessary, a small compressor can be utilized. A compressed air pressure of between 60 psig and 90 psig is adequate for permitting the sampler to operate at designed conditions.

The sampler will maintain itself free of any particulate matter, as well as fly ash that may be in the flue. The sampler can be a compact unit and thus installed directly into a flue with stack wall connections for the flow of the clean gas sample to the exterior pump and analyzer, and connections for the compressed air pass through the stack wall.

BRIEF DESCRIPTION OF THE DRAWINGS

FIG. 7 is a modified form of the sampler with valves on the exhaust passageways.

DETAILED DESCRIPTION OF THE ILLUSTRATIVE EMBODIMENTS

Figure 1:
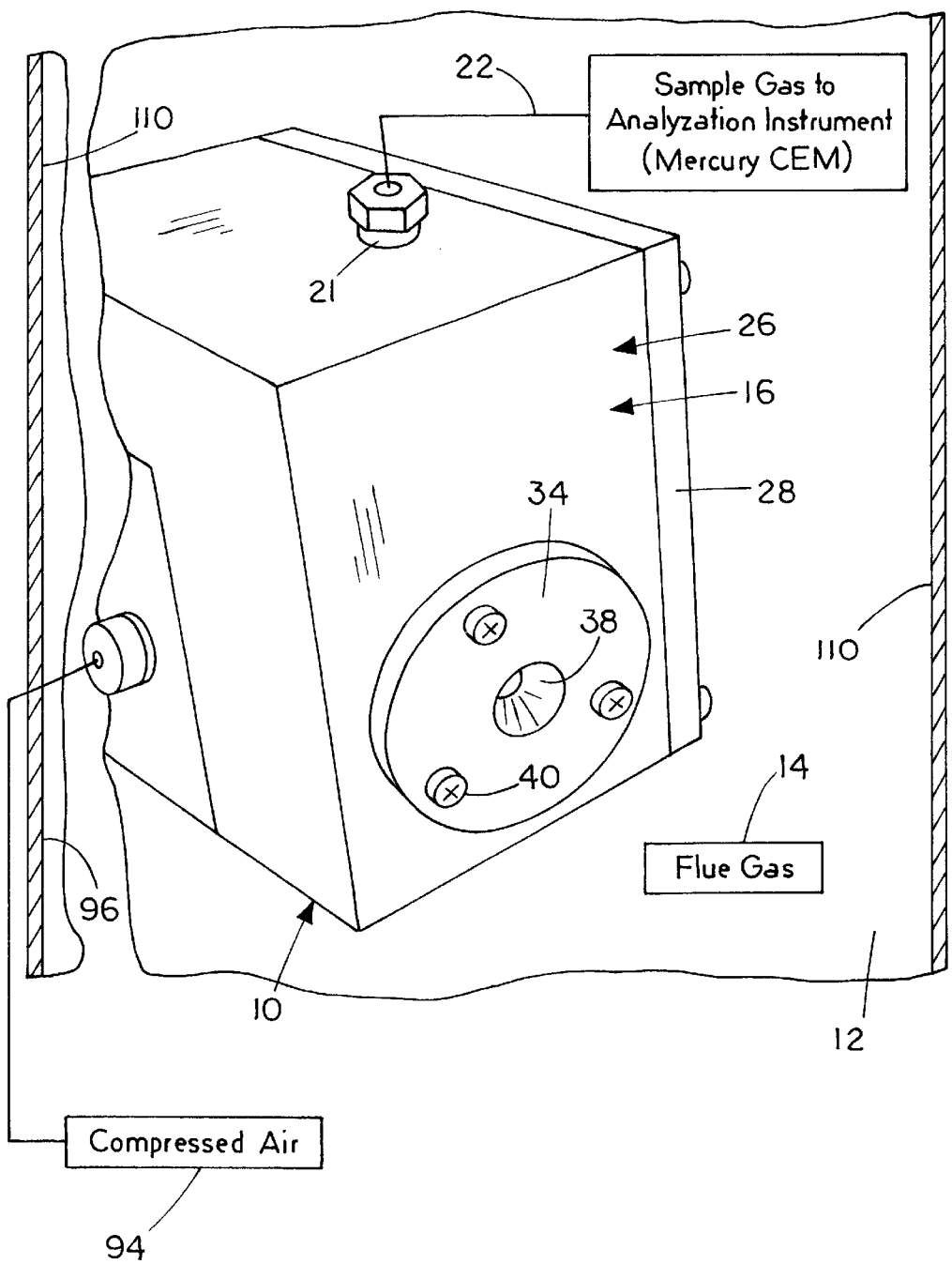
FIG. 1 is a schematic perspective view of a flue gas sampling device made according to the present invention.

The virtual impactor sampler designed for sampling flue gases is illustrated generally at 10 in FIG. 1 and, it is positioned inside a stack or flue 12 containing flue gas represented at 14. This stack or flue can be for a coal fired power plant or the like, where chemicals, such as mercury, are in the flue gas, and analyzation is desired to determine what type of control or scrubbing equipment would be effective, and to determine whether or not environmental standards are met.

The virtual impactor sampler 10 comprises a housing 16 that has internal passageways and nozzles as will be explained for removing particulate matter from the sample drawn into the sampler housing 16 from the flue 12. The sampler housing utilizes virtual impactor principles, and in a virtual impactor, a flow of a gas is induced through the housing. In the present instance, referring specifically to FIG. 5, the sampler or housing indicated generally at 16 is connected to various components, and in this instance, the flow through the housing passageways for removing the particles is provided by a sample pump 20 that has its low pressure side connected through a conduit 22 passing into the flue to a connection 21 to a chamber in the housing. The pump 20 provides the clean gas flow from the housing 16 to a mercury CEM 24. Other treatment devices, such as a chemical conversion unit 25 can be connected in the output from the sample pump 20.

Figure 2:
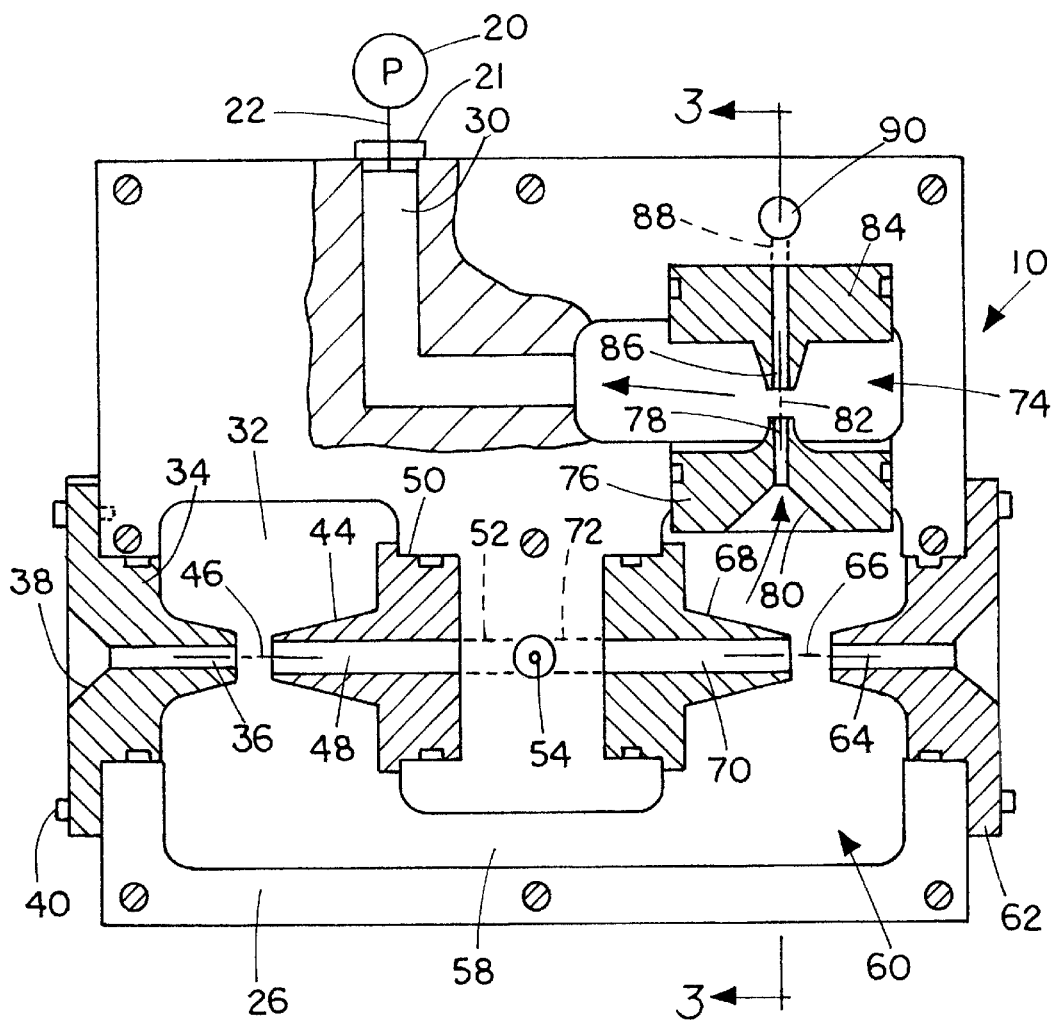
FIG. 2 is a side elevational view of the devices in FIG. 1 with a cover plate removed.
Figure 3:
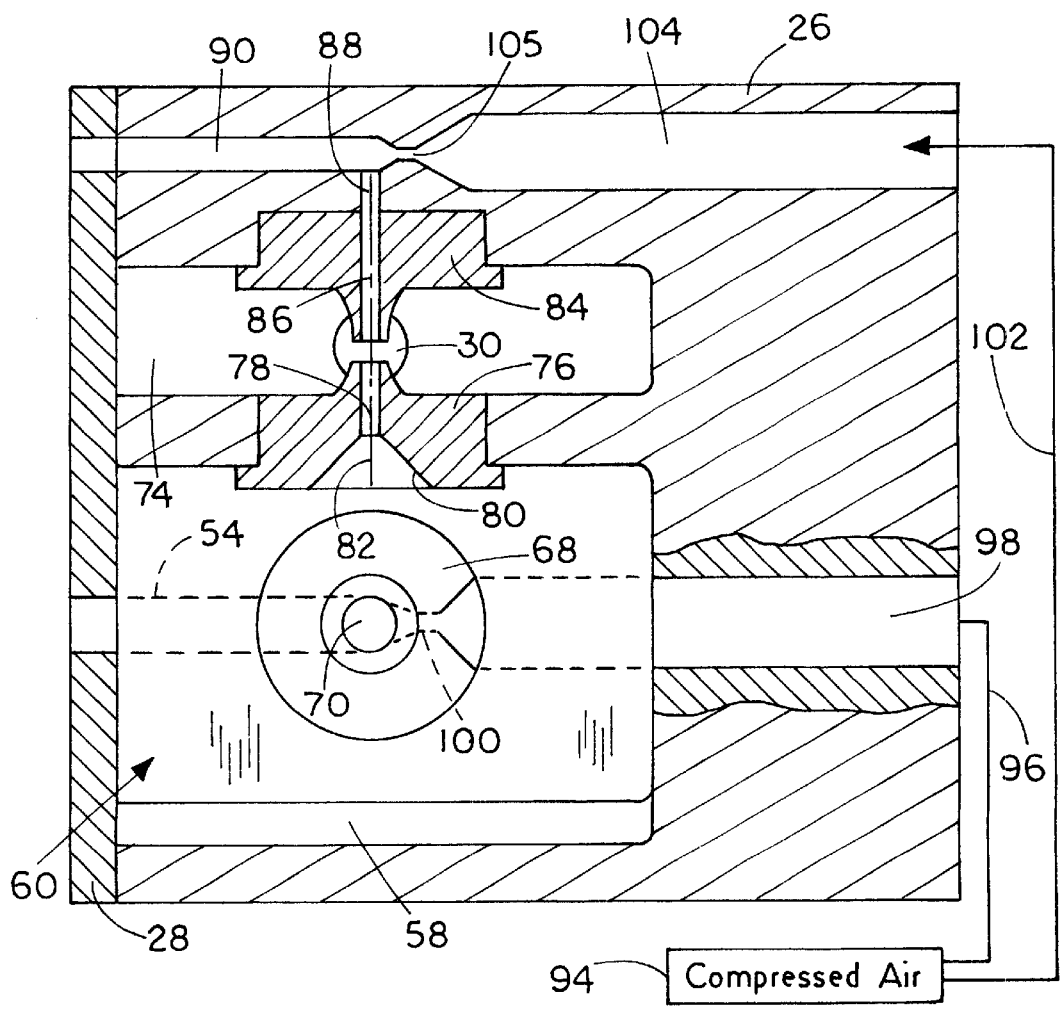
FIG. 3 is a sectional view taken as on line 3—3 in FIG. 2 with broken away portions to show both first and second exhaust passageways.

As seen in FIG. 1, the housing 16 includes a main body 26 and a cover plate 28 that covers one side of the body. The cover plate 28 is removed in FIG. 2, for sake of clarity. Referring to FIG. 2, main body 26 is shown, with various nozzles in cross section for sake of illustrating the internal passageways. The body 26 has an exhaust passage 30 that is connected to the pump 20 through line 22, as shown in FIG. 2. Pump 20, as stated, provides for a flow through the various stages of the sampler 10, and as seen, the sampler body 16 is formed with a first internal chamber 32, into which a first inlet nozzle 34 protrudes. Nozzle 34 is mounted in a suitable opening in the side wall of the housing 26, and has a central inlet passageway or tube 36, and a tapered or conical shaped inlet end 38 that is open to receive the flue gas, as shown in FIG. 1. This first inlet nozzle is removable, as can be seen, and it is held in place with suitable cap screws 40.

Figure 4:
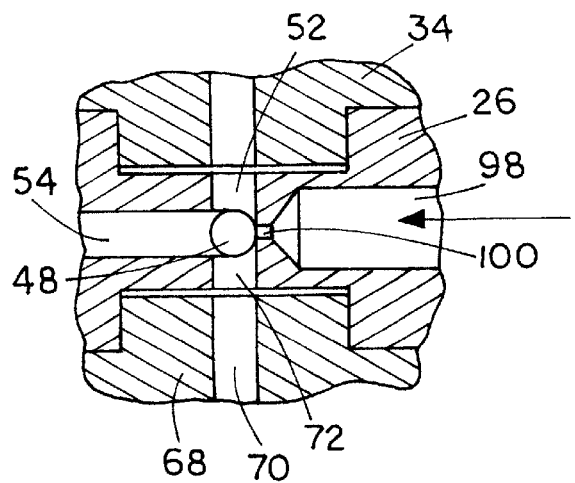
FIG. 4 is a fragmentary sectional view of a compressed air jet used with a first passageway of a first stage portion of the sampler of the present invention.

The passageway 36 of the nozzle has a central axis 46 that is aligned with a bore or passageway 48 of receiver tube or nozzle 44. The inlet nozzle interior end is spaced from the inlet end of the receiver nozzle 44. The passageway 36 and the passageway 48 are coaxial. The receiver nozzle 44 is mounted in a suitable recess or receptacle 50 formed in the housing 26. The passageway 48 also aligns with a short passageway shown in dotted lines in FIG. 2 at 52 that intersects at a cross exhaust passageway 54, as also shown in FIG. 4, to a chamber for what is called minor or secondary flow. Passageway 54 is the discharge passageway for the minor or secondary flow.

The body 26 has a second interior chamber 60 that is connected to the first chamber 32 with a cross passageway 58. The second chamber 60 also comprises a virtual impactor major flow chamber. A second inlet nozzle 62 is mounted in a provided opening in the wall of the body 26 leading to the second chamber. The inlet nozzle or inlet member 62 has a central second inlet passageway 64 with a central axis 66. A second receiver nozzle or tube 68 is mounted in a provided receptacle along the side of the chamber 60 and has a second receiver passageway or tube 70 facing the inlet passageway 64, and coaxial therewith so that the axis 66 is also the axis of the passageway or bore 70 forming the second receiver tube. The inner or outer end of the second inlet nozzle 62 and the inlet end of the second receiver nozzle 68 are spaced as well.

The receiver passageway or bore 70 aligns with a short passageway 72 that also intersects the cross exhaust passageway 54, forming a secondary flow outlet. The short connecting passageways 52 and 72 are shown in FIG. 4 as well.

The second inlet nozzle 62 has a tapered or conical inlet opening 67 leading to the passageway 64, in the same way the first inlet nozzle 34 has a conical inlet.

The first and second chambers 32 and 60 and the associated first and second inlet nozzles 34 and 62, and their first and second receiver nozzles or tubes 44 and 68 are fluidly connected together and form a double nozzle first impactor stage that causes the particles to be inertially separated and removed from the major portion of the flow through the samplers, operating as will be explained.

The main body 26 of housing 16 also has a third chamber 74 that has an opening in which a third inlet nozzle 76 is mounted. The inlet nozzle 76 has a central inlet passageway 78, and a tapered inlet surface 80 open to the chamber 60. The inlet passage 78 has a central axis 82. A third receiver nozzle 84 has a receiver tube or passageway 86 that has a central axis coaxial with axis 82. The third receiver passageway or receiver tube 86 aligns with a short passageway in the body 26 shown in dotted lines at 88 that leads to a cross minor flow exhaust discharge passage 90, forming a secondary or minor flow outlet chamber or passage.

The major flow outlet passage 30 carrying clean gas, as shown, is connected to the chamber 74, so that inlet flow from the first and second inlet nozzles minus the minor flow through receiver tube passageways 48, 70 and 86 passes through the third inlet nozzle 76, into chamber 74, and then out through the passageway 30 caused by the pump 20. This major, particle free flow then is provided to the exterior pump and analyzation instrument.

Each of the first, second and third sets of inlet nozzles and receiver nozzles or tubes operates as a virtual impactor. Because of the flow caused by pump 20, particle laden gas will enter the chambers 32 and 60, and this flow is accelerated in the inlet nozzles. The major flow or largest proportion of the inlet flow will turn or be diverted in the space between the outlet end of the inlet passageways 36 and 64 and the inlet ends of receiver passageways 48 and 70, so that the flow will turn essentially 90° across the axes 46 and 56. Because of greater inertia, particles in the inlet flow will enter into the respective receiver tubes or receiver passageways 48 and 70, and then through the passageways 52 and 72 into the cross exhaust passageway 54. The minor flow gas will pass through the receiver tube passages 48 and 70, and will carry the particle laden air out through the exhaust passage 54. The secondary or minor flow, in a normal virtual impactor is provided by a small pump that would be connected to the exhaust or discharge passageway 54. However, the minor flow may be provided in a preferred manner that also maintains the passageways free of particles as shown. A source of compressed air, indicated generally at 94 is connected with a line 96 to a compressed air passage 98 that is coaxial with the cross passage 54. An orifice 100 shown in detail in FIG. 4, is placed between the passage 98 and the exhaust passageway 54 so that the compressed air is accelerated to form a jet past passageways 52 and 72. Particles that are ejected through the passageways 52 and 72 are carried out the exhaust passageway 54. The jet provides a secondary flow through the receiver tube passageways 48, 52, 70 and 72 the jet provides an adequate secondary flow and is of sufficient velocity in the exhaust passageway 54 so that particles will not adhere to the surfaces of exhaust passageway 54, or to the nozzles.

The second stage impactor in chamber 74, is provided with a minor flow as well. Compressed air source 94 is connected with a line 102 to a passage 104 that has an end orifice 105 at its inner end that communicates with the exhaust passageway 90. This again forms a jet of air moving past the passageway 88 that carries particles into the passageway 90 and the particles are then ejected by this ejector action into the passageway 90. Both the passageways 54 and 90 discharge the particles back into the flue in which the housing 16 is mounted.

Again the second stage of the virtual impactor comprising the third inlet nozzle 76 and the third receiver tube or passageway 86 shown in nozzle 84 provides for separation of the particles, in that the flow out the passage 30 will carry the major flow from both inlets in the first stage to the pump 20 and then into the analyzation instrument. The remaining particles that are carried into passageway 78 are accelerated, and inertia will cause such particles, pass into the receiver tube 86 and then in to the exhaust passage 90.

Each of the three chambers in FIG. 2 together with the inlet and receiver nozzles contained therein form a virtual impactor. As the total flow enters the chamber through the inlet nozzle it is accelerated to a sufficiently high velocity to cause particle impaction into the receiver nozzle. Most of the total flow is deflected sideways and only a small portion of the total flow is allowed to flow through the receiver nozzle to carry away the particles. The large flow deflected sideways is relatively clean and is referred to as the major flow, and the small flow through the receiver nozzle that contains most of the particles is referred to as the minor flow. In FIG. 2, the major flow from chambers 1 and 2 are combined and form the total flow through the inlet nozzle in the third chamber where it undergoes a further stage of impaction, particle removal and cleaning before the gas is sampled into the analyzation instrument for mercury analysis.

Figure 5:
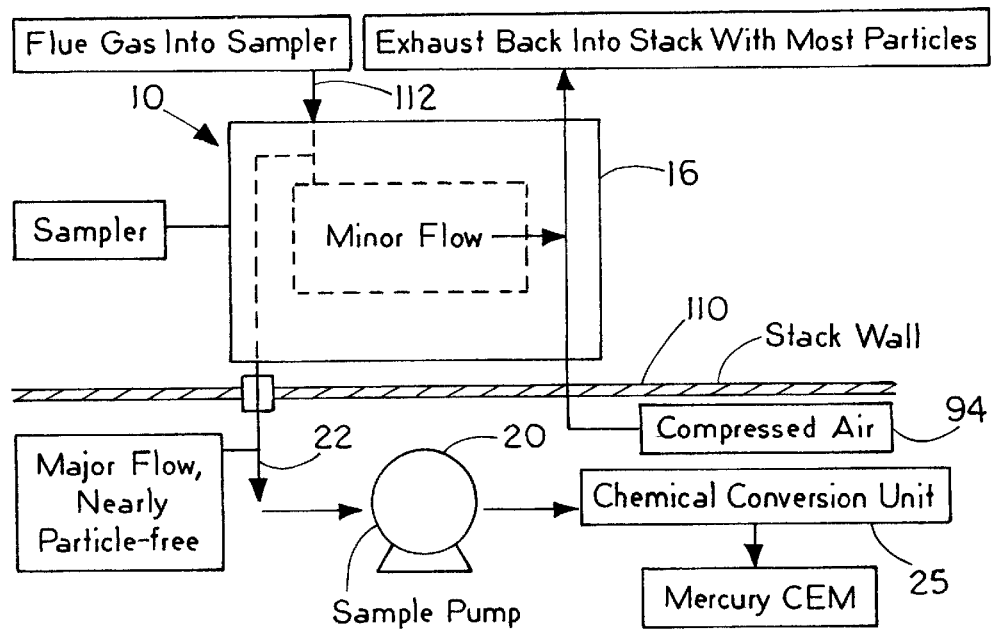
FIG. 5 is a schematic representation of a flow path used with the sampler of the present invention.

In FIG. 5, a schematic representation is shown, with the sampler 10 that utilizes the virtual impactor principles, is mounted to the interior of a flue stack wall 110. Thus the pump and the analyzation instrument can be outside the flue stack wall 110. The compressed air source 94 provides a minor flow through the exhaust passageways, previously shown, and this is exhausted back into the flue or stack with most of the particles in the sample. The particles are carried into the respective receiver tubes and then out through the exhaust passageways. A pump to establish the minor flow can also be connected to the exhaust passageways and mounted either inside or outside the flue wall.

The flue gas inlet is indicated by the arrow 112, and this inlet flow forms a major flow that is drawn through the pump 20 and is nearly particle free, as it moves through the conduit or line 22 to the exterior pump.

Figure 6:
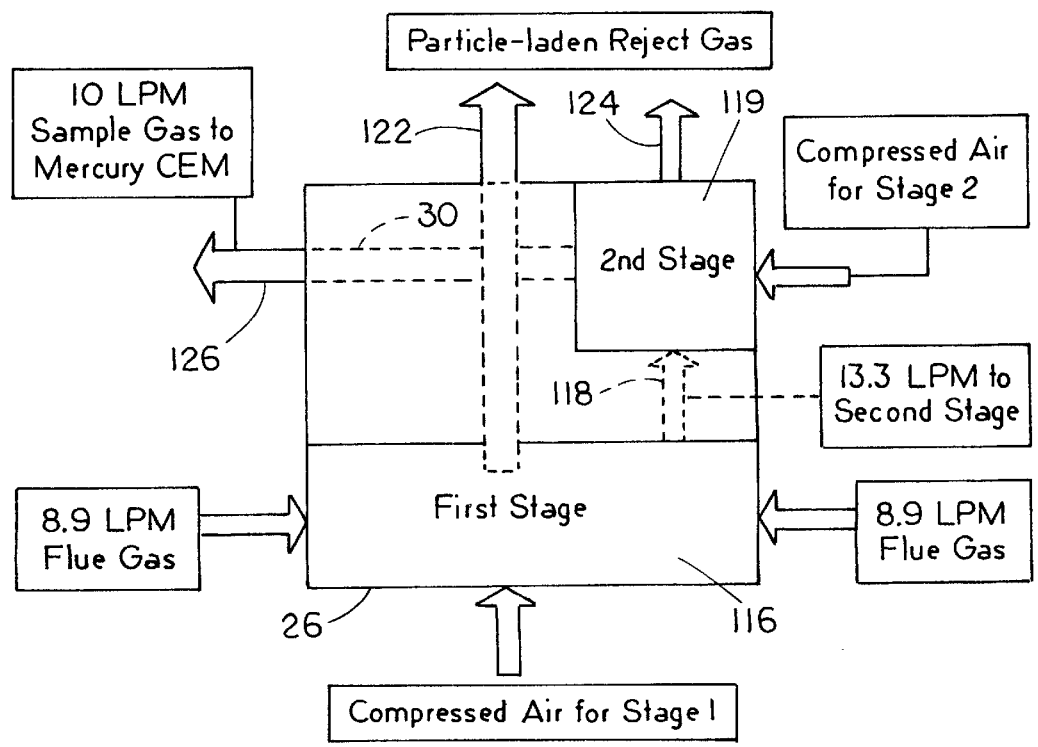
FIG. 6 is a schematic representation of the flows in a typical installation into the sampler of the present invention.

In FIG. 6, the representation of the body 26 is made. The first stage impactor is indicated at 116, and this involves two separate virtual impactor nozzles and two receivers mounted in the chambers 32 and 60. The flow to the second stage is indicated at 118. The second stage 119 is in the chamber 74. Flow into the second stage is through a passageway indicated by the arrow 118, and is essentially the inlet passageway 78 in the third inlet nozzle 76. The two discharge lines or exhaust lines that connect to the exhaust passageways are indicated at 122 and 124, respectively, and both of these comprise particle laden reject gas that in the preferred form shown goes back into the stack or flue. The major flow of sample gas that is drawn by the pump 20 then passes out, as shown, through the passageway 30, and this comprises a major flow indicated by the arrow 126.

The inlet flows are shown schematically as well, and in a particular form of the invention, approximately nine liters per minute is drawn in through both of the inlet passageways 64 and 36 in the first stage, and approximately 13.3 liters per minute are provided to the chamber 74 comprising the second stage, through the passageway 78.

The compressed air sources are shown separately in FIG. 6, and they are provided to the first stage and second stage exhaust passageways, as explained, through orifices that provide a jet ejector action.

This ejector action draws the minor flow from the virtual impactor and ejects the particles contained therein back to the flue without using a pump or blower. This is a greater advantage of the present invention, as the use of a pump or blower would greatly increase the size, volume, cost, and complexity of the sampler and reduce its operational reliability.

It should be noted that the dimensions of the orifices 100 and 105 of the exhaust passageways 54 and 90, and the point where the receiving tubes and their short connecting passageways 52 and 72 leading to the respective exhaust passageways relative to the orifices, are chosen to insure that the static pressure draws the minor flow in a venturi like effect. Once the minor flow and the expanding compressed air flow have mixed, they are exhausted out of the sampler back to the flue gas stream.

It should also be noted that the flow from the chamber 32 that passes through the passageway 54 flows around the nozzles 68 and 62, on the way to the second stage. The dimensions of the major flow chambers or plenums are much larger than the separation between the acceleration nozzles or inlet nozzles and the corresponding receiver tubes. Flow dynamics required for the separation of particles in the first stage, comprising the action in chambers 32 and 60, is unaltered by the flow of the gas to the second stage.

Another feature of the present invention is that the nozzles are interchangeable, and different size passageways can be used as is needed for different size particles that might be present in a particular stack or flue. The particles above the cut point size of the virtual impactors can be collected, and with the two nozzle first stage, that is, two inlet passageways or nozzles and two receiver tubes or nozzles, the pressure drop is kept very low.

As shown schematically in FIG. 7, a different form of cleaning can be obtained merely by placing valves in the passageways 54 and 90, that are solenoid controlled. These valves could be on the exterior, and they are shown in FIG. 7 in the cover plate 28. A first valve 130 is mounted in a portion of the passageway 90 in the cover plate 28, and a second valve 132 is mounted in the portion of the passageway 54 in the cover plate. A controller shown at 134 can be used for energizing the valves and closing them momentarily, or for a selected time, and then the compressed air coming through the orifices 100 and 105 will cause a back or reverse flow through the receiver tubes, and also then provide a flow of air across the inlet tubes, depending on the volume of flow from the compressed air source.

This will aid in cleaning the system and making sure that, the particles are not adhering to the surfaces of the sampler.

Although the present invention has been described with reference to preferred embodiments, workers skilled in the art will recognize that changes may be made in form and detail without departing from the spirit and scope of the invention.

What is claimed is:

1. A sampler for obtaining a sample of a flue gas and removing particles from the sample comprising a housing mountable within a flue carrying flue gas having particles to therein, a chamber in the housing, an inlet nozzle from the exterior of the housing to the chamber, the inlet nozzle having an inlet passageway through which flue gas will flow, a receiver spaced from the inlet nozzle and having a receiver passageway aligned with the inlet passageway, an exhaust passageway open to an outlet end of the receiver passageway and extending laterally of the receiver passageway to the exterior of the housing, an orifice defined in the housing between a compressed gas passageway and the exhaust passageway, the orifice being aligned with the exhaust passageway, a source of compressed gas connected to the compressed gas passageway to form a jet of gas exiting the orifice into the exhaust passageway and flowing laterally across the receiver passageway past the outlet end of the receiver passageway to carry particles exiting the outlet end of the receiver passageway into the exhaust passageway.

2. The sampler of claim 1, wherein the chamber comprises a first chamber, the inlet nozzle and receiver are in the first chamber, and a flow creating pump for creating a flow of gas through the first chamber that is substantially larger than the flow of gas through the receiver nozzle.

3. The sampler of claim 2, wherein said inlet nozzle and said receiver passageway comprise a first inlet nozzle having a first inlet passageway and a first receiver nozzle having the first receiver passageway, a second chamber formed in the housing, a transfer passageway between the first chamber having the first inlet and first receiver and the second chamber, a second inlet nozzle providing a flow of gas into the second chamber, a second receiver nozzle having a second receiver passageway aligned with the second inlet passageway, the second receiver passageway having a second outlet end opening to the exhaust passageway and positioned so the jet of- gas flows past the second outlet end.

4. The sampler of claim 3, wherein said second chamber carries flow from the first chamber and inlet flow from the second inlet nozzle to an opening to form a discharge passageway to discharge the flows.

5. The sampler of claim 3, wherein said housing has a third chamber, a third inlet nozzle opening to the second chamber and providing a third inlet passageway from the second chamber to the third chamber, a third receiver nozzle mounted in said third chamber and having a third receiver passageway connected to an exhaust passageway, the third chamber being open to an outlet passageway.

6. The sampler of claim 5, and an analysis instrument connected to receive the flow from the outlet passageway.

7. The sampler of claim 6, wherein said analysis instrument is a mercury CEM to analyze mercury in the gas carried by the outlet passageway.

8. The sampler of claim 5, wherein said third inlet nozzle and said third receiver nozzle lie along a substantially common third central axis, the second receiver inlet nozzle and second receiver nozzle lying along a second common axes, the second and third common axes being substantially perpendicular to each other.

9. The sampler of claim 5, wherein said first and second inlet nozzles and said first and second receiver nozzles have substantially the same diameter, and wherein the third inlet nozzle and third receiver nozzle have a smaller diameter than the first and second inlet nozzles.

10. The sampler of claim 5, wherein said first and second inlet nozzles and said first and second receiver nozzles are releasably mounted to permit replacement thereof with other nozzles having different size passageways.

11. The sampler of claim 1 including a pump for providing a pressure differential to cause flow into the inlet and from the chamber, and to cause the flow from the inlet to deflect laterally of the inlet passageway as the flow moves from the chamber.

12. The sampler of claim 1, wherein said orifice has an axis that is substantially perpendicular to a central axis of the receiver passageway.

13. A method for particle removal from a flue gas in a flue for compositional gas analysis using a virtual impactor comprising placing the virtual impactor in a flue carrying flue gas having particles therein, establishing a major flow and a minor flow in the impactor to separate particles carried in the flue gas from the major flow to provide a particle free flue gas sample and carrying the removed particles with the minor flow, removing the major flow particle free flue gas sample from the virtual impactor, and using the removed particle free flue gas sample for gas analysis.

14. The method of claim 13 including returning the minor flow to the flue.

15. The method of claim 14 including passing compressed gas from a source through a flow restriction to form a jet past a minor flow outlet of the virtual impactor to provide the minor flow.

16. A virtual impactor sampler for obtaining a sample of a flue gas from a flue having a wall and removing particles from a major portion of the sample of the flue gas, comprising a housing, a chamber in the housing, an inlet nozzle having an inlet passageway for carrying a sample of flue gas, a receiver spaced from the inlet nozzle and having a receiver passageway aligned with the inlet passageway and into which particles in the flue gas are projected by inertia, and thereby removed from a major portion of the flue gas to provide a clean flue gas sample in the chamber, a vacuum pump connected to the chamber through a conduit extending through the wall for carrying the clean flue gas sample from the chamber, an outlet of the pump being connected to an analyzer, and a passageway carrying a jet of compressed air across the receiver passageway to an exhaust passageway to establish a minor flow through the receiver passageway and to carry particles from the receiver passageway into the exhaust passageway.

17. The virtual impactor of claim 16, wherein there is an orifice positioned in the passageway carrying a jet of compressed air across the receiver passageway laterally of an outlet end of the receiver passageway.

18. A sampler for obtaining a sample of a flue gas and removing particles from the sample comprising a housing mountable within a flue carrying flue gas having particles therein, a first chamber in the housing, a first inlet nozzle from the exterior of the housing to the first chamber, the first inlet nozzle having a first inlet passageway, a first receiver spaced from the first inlet nozzle and having a first receiver passageway aligned with the first inlet passageway, an exhaust passageway open to an outlet end of the first receiver passageway, an orifice defined in the housing between a compressed gas passageway and the exhaust passageway, a source of compressed gas connected to the compressed gas passageway to form a jet of gas exiting the orifice into the exhaust passageway and flowing past the outlet end of the first receiver passageway, and a second chamber in the housing, said second chamber having a second inlet nozzle having a second inlet passageway and a second receiver having a second receiver passageway aligned with the second inlet passageway and spaced therefrom, the second receiver passageway having a second outlet adjacent the orifice and opening to the exhaust passageway, the first chamber and the second chamber being fluidly connected to permit gas flow therebetween.

* * * * *

UNITED STATES PATENT AND TRADEMARK OFFICE
CERTIFICATE OF CORRECTION

PATENT NO. : 6,561,045 B2
DATED : May 13, 2003
INVENTOR(S) : Liu et al.

It is certified that error appears in the above-identified patent and that said Letters Patent is hereby corrected as shown below:

<u>Title page,</u>
Item [57], ABSTRACT,
Line 4, after "is" delete ",".

<u>Column 7,</u>
Line 32, after "particles" delete "to".
Line 65, after "of" delete "-".

Signed and Sealed this

Fourteenth Day of October, 2003

JAMES E. ROGAN
*Director of the United States Patent and Trademark Office*